United States Patent [19]

Monzyk

[11] Patent Number: 5,304,382
[45] Date of Patent: Apr. 19, 1994

[54] FERRITIN ANALOGS

[75] Inventor: Bruce F. Monzyk, Maryland Heights, Mo.

[73] Assignee: Monsanto Company, St. Louis, Mo.

[21] Appl. No.: 835,935

[22] PCT Filed: Aug. 3, 1990

[86] PCT No.: PCT/US90/04348
§ 371 Date: Mar. 26, 1992
§ 102(e) Date: Mar. 26, 1992

[87] PCT Pub. No.: WO91/02704
PCT Pub. Date: Mar. 7, 1991

[51] Int. Cl.$^5$ ............................................. A61K 9/14
[52] U.S. Cl. ............................ 424/489; 423/161; 423/592; 423/604; 423/605; 423/606; 423/624; 423/632; 423/641; 530/400
[58] Field of Search ............. 424/489, 499; 530/400; 423/161, 592, 604–606, 624, 632, 641

[56] References Cited

U.S. PATENT DOCUMENTS

| | | | |
|---|---|---|---|
| 3,937,668 | 2/1976 | Zolle | 424/490 |
| 4,511,591 | 4/1985 | Anderson | 426/613 |
| 4,778,671 | 10/1988 | Wusirika | 423/592 |
| 5,108,597 | 4/1992 | Funkenbusch | 210/502.1 |
| 5,141,634 | 8/1992 | Carr | 210/502.1 |
| 5,173,454 | 12/1992 | Rittler | 501/5 |

FOREIGN PATENT DOCUMENTS 1174103 8/1986 Japan.
8605170 9/1986 PCT Int'l Appl..

OTHER PUBLICATIONS

International Search Report by European Patent Office.
Amendment under Article 19(1).
Written Opinion from International Searching Authority.
Price, Daniel J. Journal Biological Chemistry, vol. 28, No. 18, p. 10.
Wardeska, Jeffrey G., Journal Biological Chemistry, vol. 261, No. 15, p. 6677.
Treffry, A., Jour. of Inorganic Biochemistry, vol. 21, 9–20.
Ford et al. "Ferritin: design and formation of an iron-storage molecule", Phil. Trans. R. Soc. Lond. B 304, 551–565 (1984).
Meldrum et al. "Synthesis of inorganic nanophase materials in supramolecular protein cages" Nature vol. 349 (1991).

Primary Examiner—Thurman K. Page
Assistant Examiner—G. S. Kishore
Attorney, Agent, or Firm—Thomas E. Kelley; Mark F. Wachter

[57] ABSTRACT

Ferritin analogs comprising an apoferritin protein shell and a core substantially devoid of ferrihydrite, e.g. of inorganic composition such as aluminum hydroxide or organic composition such as acetaminophen. The protein shell can be removed from ferritin analog to produce spherules having a substantially monomodal nominal diameter between about 45 and 100 Angstroms.

3 Claims, 2 Drawing Sheets

FERRITIN ANALOGS

Disclosed herein are inventions relating to compositions encapsulated in a protein shell, more specifically such inventions comprise ferritin analogs, methods of making ferritin analogs and methods of using ferritin analogs, e.g. to produce nanosized (e.g. about 1-50 nanometers) particles and monolithic articles such as ceramics. Also disclosed are inventions relating to substantially uniform spherules of a monomodal size distribution prepared from ferritin analogs and methods of making and using such spherules.

BACKGROUND OF THE INVENTION

Among the tougher ceramic materials are those comprising ultra-small particles. Such particles are conventionally prepared by grinding larger particles and classifying the resultant mix of particles of wide ranging sizes and shapes, e.g. lumps, discs and needles, etc. The variety of shapes are difficult to separate and inhibit close packing of particles in use. For instance, when ceramics are produced from such particles, the disparate shapes provide discontinuities and stress risers which can result in failure of the ceramic article. Some attempts to produce high performance ceramics have focused on uniformity and fineness of particles. For instance, Eastman et al. in *Research and Development* pp 56-60 (January 1989) report the production of ultrafine powders of alumina, rutile etc. by condensing evaporated atoms in a low pressure inert gas, followed by compaction; the particles have a typical grain size distribution from about 5 to 25 nanometers (50-250 Angstroms). Also, Wusirika in U.S. Pat. No. 4,778,671 discloses the production of substantially unagglomerated metal oxide particles of up to about 1 micron mean diameter by precisely controlled precipitation of chelated solutes. The production of ultrafine particles of substantially monomodal size distribution has eluded practioners in the ceramics but remains an objective in efforts to provide high performance ceramics.

Substantially uniform nanosized particles are ubiquitous in nature, i.e. in the form of the mineral core of the natural iron storage molecule, commonly known as "ferritin". Although iron is essential for most forms of plant and animal life, free or too much iron can be harmful. In nature ferritin serves to accumulate, store and dispense iron in response to the flux of iron entering or leaving the plant or animal. The structure and characteristics of ferritin is discussed by Ford et al. in "Ferritin: design and formation of an iron-storage molecule", B 304 *Phil. Trans. R. Soc. Lond.* 551-565 (1984). Ferritin is characterized as a hybrid polymer comprising a protein shell, assembled from 24 structurally equivalent protein subunits, forming a nearly spherical hollow shell surrounding a hydrous ferric oxide core, commonly known as "ferrihydrite", which is reported to have a diameter of about 5-8 nanometers (50 to 80 Angstroms) which corresponds to about 4500 iron atoms. It is believed that ions permeate through intersubunit channels in the protein shell to nucleation sites on the inside surface of the protein shell where the ferrihydrite core grows from the outside in.

Since ferritin is concentrated in the spleen and liver of higher animals, horse spleen provides a common source of ferritin for many applications. Stefanini et al. in "On the Mechanism of Horse Spleen Apoferritin Assembly: A Sedimentation Velocity and Circular Dichroism Study", 26 *Biochemistry* 1831-1837 (1987), discloses disassembly in acid of ferritin into protein subunits and liberated iron core. After the iron core is dissolved in acid the protein subunits can then be reassembled to provide a hollow protein shell, commonly known as "apoferritin".

Ferritin has been proposed for a variety of uses. For instance Zimmerman et al. in U.S. Pat. No. 4,269,826 discloses the preparation of magnetic field concentratable tumor treating agents by incorporating ferritin into erythrocytes.

Shukla, et al. in *Anal. Chem. Symp. Ser.* 14 (Chromatogr. Mass. Spectrum. Biomed. Sci., 2) 179-86 (1983) discloses attempts to provide cancer therapy compounds by complexing Group IIA metals, e.g. radioactive gallium, to ferritin.

A variety of ferritin complexes with other metals have been reported from studies of metal binding to ferritin and apoferritin. For instance, Price et al. in *J. Biol. Chem.* 258(18), 10873-80 (1983) report the binding of cadmium, zinc, copper and beryllium to ferritin and apoferritin. Treffry et al. in *J. Inorg. Biochem.* 21(1) 9-20 (1984) report studies of low level binding of terbium and zinc to apoferritin, e.g. about 24 atoms per apoferritin. Wardeska et al. in *J. Biol. Chem.* 261(15) 6677-83 (1986) report the low level binding of cadmium, manganese, terbium, vanadium and cadmium to apoferritin, e.g. less than about 2 metal atoms per apoferritin subunit.

Price et al. in J. Biological Chemistry 258 (18) pp 10873-80 (1983) report (in Table I) that ferritin can be saturated with low levels of metals, e.g. 175 g-atoms of zinc and cadmium, 58 g-atoms of copper (I): and that apoferritin bound even lower levels of those rates, e.g. 71 g-atoms of cadmium, 36 g-atoms of zinc and 50 g-atoms of copper.

OBJECTS OF THE INVENTION

An object of this invention is to provide ultrafine particles which are useful in the production of high performance ceramics.

Another object is to provide such particles having a substantially equiaxial shape and monomodal size distribution.

Another object is to provide precursors of such particles having a protein coating that inhibits agglomeration of such particles.

Other objects include the provision of variations of such ultrafine particles for ceramic as well as divers other applications, methods for using such particles including precursors of such particles and processes for preparing such particles. These and other objects of the invention will be more readily apparent from the following detailed description.

SUMMARY OF THE INVENTION

Despite the fact that ferritin is extremely selective in accumulating, storing and dispensing iron in living things, I have discovered that the forgoing objectives can be realized by inserting any of a variety of compositions into apoferritin at unexpectedly high purity and concentration to provide ferritin analogs. Such ferritin analogs comprise a core which is substantially devoid of ferrihydrite, the natural core of ferritin. For some applications the protein shell of the ferritin analog serves as an advantageous encapsulant for the core material, e.g. an organic or inorganic spherule, concentrated solution or other material. For other applications it may be desirable to remove the protein shell from the ferritin analog to recover the core material as a spherule. I have discovered that the protein shell can be advantageously removed, e.g. by partial or complete pyrolysis in the case of inorganic spherules or by subjecting the ferritin analog to an environment which causes disassembly of the protein shell, e.g. low or high pH. Partial pyrolysis can provide carbon-coated spherules useful, e.g. for ceramic applications. Such spherules have a substantially monomodal, nominal diameter typically in the range of about 4.5-9 nanometers (45 to 90 Angstroms); such monomodal spherules can be advantageously grown substantially monomodally to even larger spherules or agglomerates of spherules, e.g. up to about 20 nanometers (200 Angstroms) or larger, say about 300 nanometers (3000 Angstroms). I have also surprisingly discovered that monolithic articles prepared from inorganic spherules have unique properties, e.g. ceramics can be prepared at substantially lower sintering temperature, with substantially uniform shrinkage and with smaller surface flaws.

DETAILED DESCRIPTION OF THE INVENTION

Throughout this specification, percentages of compositions are by weight and temperatures are in degrees Celsius unless indicated otherwise.

As used in this specification and the appended claims, the term "spherule" means a particle having a generally spherical shape and particles comprising spherical segments such as hemispherical particles. Spherules grown in apoferritin can be substantially completely full or may be partially full, e.g. hollow spherules or segmented spherules.

As used in this specification and the appended claims, the term "ferritin analog" means a hybrid composition comprising an apoferritin shell surrounding a core substantially devoid of ferrihydrite. For instance, an aluminum ferritin analog has a core comprising an aluminum compound, e.g. aluminum sulfate or aluminum hydroxide; similarly, an acetaminophen ferritin analog has a core comprising acetaminophen.

As used in this specification and the appended claims, the term "ferritin" means a protein that has biological and/or chemical activity and structure the same as, or substantially similar to, a natural ferritin. Natural ferritins comprise human ferritin and other animal ferritin, e.g. derived from horse spleen, phytoferritin, e.g. derived from cow pea leaves, myco ferritin, e.g. derived from fungi, or bacterial ferritin including ferritin expressed by genetically-transformed microorganisms such as E. coli, and other bacteria and yeasts. Bacteria-expressed ferritin may have an amino acid sequence identical or analogous to a natural ferritin. An analogous amino acid sequence will have one or more variations in amino acid sequence which may provide enhanced deposition of non-ferrihydrite cores or some other advantage.

As used in this specification and appended claims the term "apoferritin subunit" means one of the 24 structurally similar basic protein units that combines to form the protein shell of a ferritin molecule. Apoferritin subunits can also comprise combinations of such basic subunits, e.g. dimers and octamers of such subunits and other partially assembled apoferritin protein shells.

As used in this specification and the appended claims, the term "sterile-filtered" means a solution which has been passed one or more times through a 0.2 micron filter, e.g. as available from Millipore Corp., to remove dust, bacteria and other microbes that may adversely effect the protein solutions; except as stated herein, all solutions used to process protein are sterile-filtered.

The ferritin analogs of this invention comprise a core substantially devoid of ferrihydrite, the natural iron core material of ferritin. In some cases ferritin analogs may advantageously be essentially devoid of ferrihydrite; in other applications it may be useful or advantageous for ferritin analogs to contain trace amounts of ferrihydrite. In other cases the ferritin analog may contain more than a trace amount of ferrihydrite, e.g. a composite core comprising a ferrihydrite outer layer over a different material.

Ferritin analogs according to this invention can have cores of a variety of compositions, e.g. substantially inorganic compounds, substantially organic compounds inorganic/organic complexes, or mixtures thereof. Such cores can comprise solid spherules, e.g. of crystalline or amorphous inorganic or organic compounds such as aluminum hydroxide, or concentrated solutions, e.g. of organic materials such as sugars. Depending on the composition and state, i.e. solid or liquid, of the core, ferritin analogs can be useful for divers applications. For instance, ferritin analogs useful in high performance ceramics can have inorganic cores, e.g. of aluminum hydroxide spherules, magnesium oxalate spherules and the like. Ferritin analogs useful for nutrition products can have organic cores, e.g. mineral spherules of potassium iodide, or organic cores, e.g. concentrates of vitamins or flavorings such as vanillin, spherules of a sugar or other sweetener such as aspartame. Ferritin analogs useful as biocompatible delivery systems for therapeutic and/or diagnostic materials can have cores comprising analgesics and/or non-steroid anti-inflammatory agents such as acetaminophen, aspirin and ibuprofen.

Chemotherapy agents are often deleterious to tissue, e.g. blood vessels, due to toxic concentrations of parenteral injections. A biocompatible protein shell of a therapeutic ferritin analog can provide an advantageous method of protecting tissue from the locally toxic effect of parenterally injected therapeutic agents, e.g. chemotherapy compounds.

An inorganic core of a ferritin analog can comprise a variety of inorganic species, e.g. metal salts, metal oxides, metal hydroxides, non-metal oxides and the like. Monovalent metals, e.g. potassium and silver, can be used advantageously in ferritin analogs of this invention. For instance, potassium iodide ferritin analogs can be useful as an oral delivery system for therapeutic doses of potassium iodide. Silver chloride ferritin analogs can be useful for generating nanosized spherules of silver chloride, a photosensitive material. Polyvalent metal ferritin analogs are useful for many other applications including the generation of nanosized spherules of polyvalent metal compounds. Polyvalent metals preferred for use in many such applications include aluminum, ammonium, barium, chromium, cobalt, copper, europium, gadolinium, lanthanum, magnesium, manganese, neodymium, titanium, uranium, ytterbium, yttrium, zirconium and the like. In some cases the polyvalent metal can comprise iron which, except as indicated above, is in a composition substantially other than ferrihydrite, e.g. as a sulphate or a different oxide such as magnetite. For some applications it is desirable that the particle comprise an oxide, hydroxide or a hydrated oxide. For other applications it is desirable that the nonosized spherule comprise a salt of an anion such as acetate, bromide, carbonate, chloride, fluoride, iodide, nitrate, nitrite, oxalate, phosphate, phosphite, sulfate, sulfide or sulfite or a mixture thereof, including mixtures with oxides and hydroxides. Organic materials comprising ferritin analog cores can also be present as salts, e.g. aspirin ferritin analog can be present as the precipitated salt of acetylsalicylic acid.

Novel and preferred ferritin analogs of this invention which are advantageously useful in providing certain ceramics of enhanced properties include aluminum ferritin analogs, i.e. ferritin analogs having an inorganic core of an aluminum compound such as an oxide, hydroxide, chloride, nitrate, sulphate, etc. or a mixture thereof. Other ferritin analogs useful for ceramic applications are magnesium ferritin analogs, i.e. having a magnesium oxalate core.

Ferritin analogs can be prepared by combining apoferritin with a non-ferrihydrite-forming solute, e.g. a solute which will not permeate into apoferritin to form ferritin. Apoferritin subunits are advantageously provided from any of a variety of sources of ferritin. Among the more economic natural sources of ferritin are horse spleens and cow pea leaves. A preferred source of apoferritin subunits is expression from genetically transformed microorganisms such as *E. coli*. Apoferritin for use in the production of ferritin analogs is advantageously provided by extraction of ferrihydrite from ferritin or assembly of apoferritin subunits.

Ferrihydrite can be extracted from ferritin into a dialysis solution comprising iron reducing agent which reduces iron(III) to iron(II) and a iron sequestering agent which effectively removes iron(II) from solution. An effective iron reducing agent is sodium hydrosulfite; an effective iron sequestering agent is ethylenediamine tetraacetic acid (EDTA). Apoferritin prepared by such extraction can contain minor amounts of residual ferrihydrite depending on the effectiveness of the dialysis procedure.

A convenient method of providing apoferritin from ferritin is disclosed by Stefanini et al. in *Biochem* 26, page 1831 (1987), incorporated herein by reference. In this method an aqueous medium containing ferritin is adjusted with acid to about pH 2 to disassemble the ferritin into protein subunits (believed to be as dimers) and ferrihydrite core. As the ferritin disassembles and the ferrihydrite dissolves the medium turns from orange to yellow. Although it is preferred to minimize exposure of the protein units to low pH to avoid the possibility of hydrolysis of the peptide bonds, I have discovered that faster disassembly can occur if the ferritin is shocked, e.g. by initially acidifying a ferritin solution to about pH 1 for about a minute or so, up to about 30 minutes, then adjusting to about pH 2. After disassembly the medium is adjusted to about pH 4 and the subunits are separated from dissolved iron, buffer compounds and other low molecular weight solutes by ultra-filtration, e.g. with a 10,000 molecular weight cutoff (MWCO) membrane which can effectively retain the relatively high molecular weight apoferritin subunits. Higher purity apoferritin can be achieved with multiple washings and ultrafiltration. The assembly of apoferritin subunits is pH dependent with some assembly occurring at pH 4. The soluble protein-containing retainate can be adjusted to about pH 7.8 to essentially complete assembly of the subunits into apoferritin. Depending on the number and efficiency of the washings, apoferritin produced by this procedure can be used to make ferritin analogs essentially devoid of ferrihydrite.

I have found that the time for reassembly into apoferritin is dependent on the time that apoferritin subunits are subjected to low pH. I have correlated that the time needed for about 90 percent reassembly at pH 7.8 is about an order of magnitude longer than the time the apoferritin subunits are maintained at pH 1.8-2. Thus, protein units maintained at pH 1.8 for two hours would require about one day for reassembly. In cases of long duration reassembly, a preservative is preferably used to prevent microorganisms, e.g. bacteria, from damaging the apoferritin subunits and/or assembled apoferritin. Preferably, such a preservative should not adversely affect the protein components in the reassembly medium. A preferred preservative is chlorotone, i.e. the base catalyzed adduct of chloroform and acetone, which is odorless, has low toxicity, is non-chelating, i.e. does not sequester metals, does not bind to charged groups on the apoferritin subunits and is effective at low concentrations, e.g. about 0.01 percent.

Once ferrihydrite is free of its protein shell at low pH, it has essentially no tendency to reincorporate into the protein. However, the ferrihydrite does tend to solubilize at low pH, generating iron ions which can bind to protein units. For those applications where it is preferred to have apoferritin essentially free of all iron, the use of a chelating agent, e.g. diethylenetriaminepentaacetic acid (DTPA), and/or a reducing agent, e.g. 2-mercaptoethanol (2-MCE), is effective in inhibiting the reincorporation of iron into apoferritin.

The reassembly of apoferritin from protein units can be inhibited by anions such as chloride and phosphate which are believed to bind to cationic sites on the protein units. Removal of such binding anions and anionic chelants and buffers by washing is believed to be advantageous for efficient reassembly of apoferritin subunits. Reassembly of apoferritin subunits into apoferritin is advantageously carried out in a medium containing certain diffuse species including anions such as acetate ions, amino acids such as glycine and non-complexing buffers such as HEPES; such species are useful for controlling pH and do not adversely inhibit reassembly especially when present in dilute concentrations.

I have discovered that ferritin analogs can be effectively prepared by allowing a non-ferrihydrite-forming solute to permeate into apoferritin in an aqueous medium buffered with a protein compatible compounds such as HEPES or ammonium acetate. The variety of protein-compatible compounds generally allows the selection of a buffer which will not adversely interfere with particle growth in the ferritin analog. Apoferritin is added to an aqueous medium which is buffered to a pH between about 4 and 8. At low pH, e.g. about 2 or 3 and at high pH, e.g. about 9, apoferritin tends to disassemble into apoferritin subunits. Apoferritin also tends to precipitate from solution at its isoelectric points, e.g. pH 6.5 for apoferritin from horse spleen. Choice of pH of the aqueous medium is also often influenced by the solubility of the material to be permeated into the apoferritin. For many applications, ferritin analogs are advantageously produced in aqueous medium buffered at pH 4–4.5. Aqueous ammonia and acetic acid are effective materials for adjusting pH of aqueous medium containing apoferritin.

The concentration of apoferritin is maintained sufficiently dilute, i.e. less than about 30 g/l, to avoid precipitation of apoferritin since it is believed that solutes permeate at lower rates into precipitated apoferritin and at faster rates into dissolved apoferritin.

A variety of compositions can be permeated from solute into apoferritin. It is believed that ionic groups on the inside surface of apoferritin provide nucleation sites for precipitation of a permeating species. Thus, mass transfer of solutes into apoferritin can be effected by providing a concentration gradient across the apoferritin shell. It is believed that saturated, or preferably supersaturated, solutes are effective for expeditions growth of cores in apoferritin. Since precipitation of solute on nucleation sites outside of apoferritin is believed to be counter productive to core growth, it is generally desirable that the aqueous medium be free of solids, e.g. precipitated apoferritin, precipitated solute, dust, bacteria, etc. The concentration of solutes in the aqueous medium is desirably maintained at saturation or supersaturation levels as core growth in the apoferritin depletes solute in the aqueous medium. The number of molecules of solute that can permeate apoferritin and provide a ferritin analog core will vary depending on a variety of factors, e.g. the molecule and its crystal structures in the ferritin analog, etc. Solute concentration can be maintained by adjusting temperature of the aqueous medium according to a temperature solubility curve for the solute, by addition of solute, or by other means well known to those skilled in the art of crystal growth, e.g. pH adjustment. Core growth can often be accelerated by increasing the temperature of the medium. Moderate temperatures, e.g. about 20°–40° C., are advantageous to avoid adverse thermal effects on the apoferritin molecule. Permeation times on the order of a day or so, say up to about 3 days, are generally sufficient to provide ferritin analogs with filled cores.

The amount of material forming a core of a ferritin analog can vary depending on whether full cores are desired. In this regard, it is believed that core growth begins on the inside of the protein shell effectively forming a hollow spherules which grow inward filling its core as solute permeation continues. It has been observed that the outside diameter of the core can vary, e.g. in the range of about 4.5–9 nanometers (45 to 90 Angstroms), depending on the material comprising the core.

It is also possible to provide a ferritin analog with a multi-component core, i.e. by changing the composition of the solute as core growth proceeds or by using a multicomponent solute.

Ferritin analogs can be recovered from the aqueous medium by ultrafiltration e.g. through a membrane having a sufficiently high molecular weight cutoff to retain ferritin analogs. For instance, membranes having a 100,000 MWCO are effective for recovery of soluble ferritin analogs. Ferritin analogs have also been observed to precipitate, e.g. analogs may have different solubility parameters than apoferritin. Precipitated ferritin analogs can be recovered, e.g. by centrifugation, filtration, settling and/or ultrafiltration. Precipitation of ferritin analogs can be induced by increasing the concentration, e.g. by ultrafiltration, pH adjustment to an isoelectric point, salting out with ammonium sulfate, cadmium-induced crystallization, cooling, and other commonly used methods.

Ferritin analogs can be used as recovered with the apoferritin shell which can be useful in preventing agglomeration or deterioration of the core or even to provide a biocompatible encapsulant encapsultant for in vivo delivery of therapeutic or diagnostic amounts of the core material. Ferritin analogs can also be fabricated into useful monolithic articles. For instance, aluminum ferritin analogs can be formed into a green ceramic precursor comprising mineral spherules in a protein binder matrix. Silver ferritin analogs can be fabricated, e.g. cast and dried, into photosensitive sheets having nanosized particles of silver compound in an ordered array. Drug ferritin analogs can be fabricated into thin, e.g. monolayer, sheets which can be used for controlled delivery to a surface requiring extended administration of a drug. Depending on the nature of the core, the apoferritin shell can be removed from ferritin analog comprising the monolithic article to provide a monolithic article comprising essentially the core of the ferritin analog. For instance, monolithic articles comprising aluminum ferritin analogs can be heated to remove the apoferritin shell, leaving a monolithic article comprising alumina spherules which can be sintered to provide a ceramic article. In other cases the apoferritin shell can be removed from the core of the ferritin analog to provide nanosized spherules by subjecting the ferritin analog to an environment in which the protein disassembles into apoferritin subunits allowing recovery of the core spherules, e.g. by ultrafiltration. Such environments can be at low or high pH and can be similar to those used to produce apoferritin. Such apoferritin subunits can be advantageously recycled for further production of ferritin analog or spherules.

Inorganic spherules prepared from ferritin analogs have unique properties commending their use in ceramic applications. For instance, alumina spherules prepared from aluminum ferritin analog has been observed to sinter at surprisingly low temperatures. Alumina conventionally sinters at about 1500° C. Lower sintering temperatures, e.g. about 1200° C., have been reported by the use of dopants or fines. I have surprisingly discovered that alumina spherules prepared from aluminum ferritin analog of this invention readily sinter at temperatures in the range of 1000°–1100° C. or lower, e.g. as low as about 700° C. Thus, alumina spherules according to this invention have been shown to be useful in providing smooth coatings on the microscopically rough surface of alumina articles by coating the alumina article with alumina spherules of this invention which sinter at temperatures below the sintering temperature of the substrate article.

The following description defines materials used in the following examples:

DI water is deionized water which has been passed through activated carbon to remove organic materials and 0.2 micron filters to remove dust, bacteria and other potentially deleterious microparticles.

pH 4 BUFFER is 0.5M ammonium acetate/acetic acid buffer at pH 4.0 filtered at 0.2 micron.

pH 4.5 BUFFER is 0.5M ammonium acetate/acetic acid buffer at pH 4.5 filtered at 0.2 micron.

HEPES is buffer solution of N-2-hydroxyethylpiperazine-N'-2-ethanesulfonic acid, pKa=7.55 at 20° C., available from Behring Diagnostics Division of American Hoechst Corporation as an ULTROL brand buffer.

FERRITIN SOLUTION is a sterile-filtered solution of horse spleen ferritin at 100 mg/ml obtained from Sigma Chemical Company, St. Louis, Mo., identified as "F4503 Ferritin, Type 1 from Horse Spleen".

The following disclosure is provided to illustrate specific embodiments and aspects of this invention but does not imply any limitation of the scope of the invention.

EXAMPLE 1

This example illustrates the preparation of apoferritin from horse spleen ferritin.

5 ml of a sterile-filtered solution of FERRITIN SOLUTION, adjusted to pH 3.5 with HCl was added to a stirred, room temperature solution comprising 2.8 g of glycine, 1.0 g of DTPA and 0.9 g of 2-MCE in 150 ml of DI water. Concentrated HCl was added to lower the pH to 2 to cause the ferritin to disassemble into apoferritin subunits and ferrihydrite particles. After stirring the medium for about 4.75 hours, the color of the medium turned yellow and the pH increased to about 3, indicating ferrihydrite dissolution. The pH was adjusted to about 4 with about 10 ml of 5M ammonium acetate. The medium was reduced to about 50 ml by ultrafiltration using a 10,000 MWCO stirred-cell ultrafiltration membrane (AMICON model YM10). A 50 ml residual volume was washed five times with 200 ml of a 0.01M acetic acid/ammonium acetate buffer solution of pH 4.1, reducing each washing by ultrafiltration to a 50 ml residual volume. Analysis of the last filtrate indicated no detectable residual chloride ions. 1 g of HEPES was added to the final 50 ml residual volume and the pH was adjusted to 7.8 with about 0.5 ml of concentrated ammonium hydroxide to provide a reassembling medium. A preservative, 2% chlorotone in DI water, was added to provide about 0.02% chlorotone in the medium which was stirred at room temperature for about 48 hours and then centrifuged. Analysis of the supernatant indicated substantial yield of apoferritin useful for preparing ferritin analogs essentially devoid of ferrihydrite. Transmission electron microscopy (TEM) showed the apoferritin to have an inside shell diameter of about 6 nanometers (60 Angstroms) and an outside shell diameter of about 12 nanometers (120 Angstroms).

Quantities of apoferritin were prepared by essentially the method indicated above providing supernatant which was sterile filtered to provide stock solutions of apoferritin, concentrated to about 20–25 mg/ml, buffered at pH 7.8 with 20 mM HEPES, and stabilized with 0.02% chlorotone (identified in subsequent examples herein as APOFERRITIN SOLUTION).

EXAMPLE 2

This example serves to illustrate an alternate method of producing apoferritin by extraction of ferrihydrite into dialysis solutions, e.g. comprising an iron reducing agent, e.g. sodium hydrosulfite, and an iron sequestering agent, e.g. EDTA.

The following dialysis solutions (DS) were prepared, e.g. with nitrogen sparging to avoid air oxidation of hydrosulfite:

| | |
|---|---|
| DS-1: | 1 M ammonium acetate |
| | 172 mM sodium hydrosulfite |
| | 30 mM EDTA |
| | pH 4.8 |
| DS-2: | 20 mM ammonium HEPES, pH. 7.8 |
| | 30 mM EDTA |
| DS-3: | 20 mM ammonium HEPES, pH 7.8 |

Equal volumes of FERRITIN SOLUTION (100 mg/ml) and DS-1 were charged to a 10–14,000 MWCO dialysis membrane and dialyzed for 24 hours 7 times against 67 volumes of DS-1; then dialyzed once for 24 hours against 67 volumes of DS-2 then dialyzed twice for 24 hours against 67 volumes of DS-3 then sterile filtered to provide APOFERRITIN SOLUTION.

EXAMPLE 3

This example illustrates a preferred preparation of an aluminum ferritin analog essentially devoid of ferrihydrite.

4 l of pH4.5 BUFFER was charged to a 5 l glass reactor and heated to 40° C.; 56.4 ml of aluminum nitrate solution (44.3 g/l Al) was added dropwise to the reactor; and 350 ml of sterile-filtered 26 mg/ml APOFERRITIN SOLUTION was added dropwise to the reactor; the pH was adjusted from 4.09 to 4.5 using concentrated ammonium hydroxide; after 10 minutes of stirring the cloudy solution became clear; an additional 169.4 ml of aluminum nitrate solution was added dropwise; pH was further adjusted from 3.86 to 4.5 with ammonium hydroxide; the solution was allowed to cool to room temperature and stirred for about 3 days; the mixture was reduced by ultrafiltration from about 4.5l to about 125 ml; analysis of the permeate and supernatant indicated that 2624 aluminum atoms were associated with each molecule of apoferritin charged; analysis further indicated that protein shells of the apoferritin were substantially filled with aluminum nitrate and hydroxide, i.e. an aluminum ferritin analog.

EXAMPLE 4

This example illustrates the separation and recovery of aluminum compound spherules and apoferritin from aluminum ferritin analog.

The procedure of example 2 was essentially followed to produce 137 g of concentrated slurry of aluminum ferritin analog; 135 ml of concentrated aqueous ammonia was added to the ferritin analog slurry; the resulting mixture was stirred and heated to about 50 C for 20 minutes to disassemble the ferritin analog into apoferritin subunits and aluminum compound spherules; the mixture was then centrifuged initially for 30 minutes at 7500 rpm resulting in a slightly cloudy supernatant and finally for 20 minutes at 10,000 rpm resulting in a clear supernatant of apoferritin subunits and a white gel sediment of aluminum compound spherules; the supernatant (which was essentially aluminum free) was decanted into a 2M ammonium nitrate solution providing a solution at pH 9; analysis of the ammoniated protein solution by size exclusion high pressure liquid chromatography (SE-HPLC) using a Pharmacia Superose-12 column indicated that apoferritin subunits had reassembled into apoferritin; the white gel sediment was determined by transmission electron microscopy to be spherules having a substantially monomodally nominal diameter of about 5 nanometers (50 Angstroms).

EXAMPLE 5

This example illustrates another preparation of an aluminum ferritin analog, i.e. aluminum hydroxide ferritin analog, by infusing aluminum sulfate into apoferritin.

84 ml of aluminum sulfate solution (29.4 mg/ml Al) was added to 4 l of pH4 BUFFER heated to 40 C. in a 5 l jacketed, stirred glass reactor to 40 C.; the mixture was stirred for 50 minutes to provide a clear, colorless solution; 350 ml of APOFERRITIN SOLUTION (25.65 mg/ml) was slowly added to the reactor over 108 minutes providing a slightly cloudy solution; 752 ml of aluminum sulfate solution (29.4 mg/ml Al) was slowly and continuously added over 140 minutes. The total aluminum added was about 10 times theoretical, i.e. the amount required to fill the total amount of apoferritin shells in the reactor. When the aluminum added was about 2.5 times theoretical, the solution became very cloudy, indicating some protein precipitation from solution. The pH of the reactor contents was adjusted from 3.5 to 4.07 with concentrated aqueous ammonia; the mixture was stirred for 2 days at room temperature.

After 1 day a 10 ml sample of the reactor mixture was centrifuged to provide a supernatant containing aluminum sulfate solution and soluble aluminum ferritin analog; the supernatant was ultrafiltered to separate aluminum ferritin analog; analysis of the permeate containing only aluminum sulfate and the retainate containing aluminum sulfate and aluminum ferritin analog indicated that on average each aluminum ferritin analog contained about 3800 aluminum atoms per apoferritin shell. Analysis after 2 days indicated further infusing of aluminum into the ferritin analog with the average aluminum ferritin analog containing about 5500 aluminum atoms per apoferritin shell.

After 2 days 4.5 l of the reactor mixture was centrifuged for 30 minutes at 7500 rpm providing about 4.2 l of supernatant containing soluble aluminum ferritin analog and about 200 g of white gel sediment of aluminum apoferritin analog; electron microscopy indicated that the apoferritin analog ranged from nearly empty apoferritin shells (believed to be apoferritin that had precipitated from the solution before substantial infusing of aluminum) to substantially full (i.e. of aluminum hydroxide) apoferritin shells. The supernatant was concentrated by ultrafiltration using a 100,000 MWCO spiral cartridge ultrafilter (AMICON YM100) to retain 350 ml of concentrated aluminum ferritin analog which was further concentrated with a 400 ml stirred-cell 100,000 MWCO membrane to 200 ml of aluminum ferritin analog gel (13% dry basis aluminum ferritin analog).

EXAMPLE 6

This example illustrates another preparation of an aluminum ferritin analog, i.e. aluminum hydroxide ferritin analog, by infusing aluminum chloride into apoferritin.

The procedure of Example 4 was essentially followed except 70 ml of aluminum chloride solution (35.8 mg/ml Al) was added to the pH4 BUFFER, followed by 350 ml of APOFERRITIN SOLUTION (26.03 mg/ml) and then 627 ml of the same aluminum chloride solution. Total aluminum again was at 10 times theoretical. The pH of the reactor contents was adjusted from about 2 to 4.14 with concentrated aqueous ammonia; the mixture was stirred for 3 days at room temperature then centrifuged providing a supernatant which was devoid of aluminum ferritin analog and a clear gel sediment of aluminum ferritin analog containing about 11,000 aluminum atoms per apoferritin shell. The core of the ferritin analog was substantially aluminum hydroxide with minor amounts of aluminum chloride. Substantial amounts of the chloride were removed by repeated (i.e.

5) washings with DI water. The washed gel was dried in a nitrogen-purged vacuum oven at about 120 C. for 1 day resulting in about 93% weight reduction from water liberation. The dried product was substantially anhydrous, chloride-free aluminum hydroxide ferritin analog.

EXAMPLE 7

This example illustrates the use of aluminum ferritin analogs to prepare alumina spherules.

Aluminum hydroxide ferritin analog recovered as a gel was dried at about 100° C. into a protein matrix sheet which was ground using a mortar and pestle into a powder. The aluminum ferritin analog powder was dehydrated at about 250° C. The dehydrated aluminum ferritin analog was charred at about 400° C. producing carbon-coated alumina spherules. At about 550° C. the carbon burned off producing gamma-alumina spherules. At about 750° C. the gamma-alumina spherules were converted to delta-alumina. At about 1050° C. the delta-alumina spherules were converted to alpha-alumina spherules.

EXAMPLE 8

This example illustrates the preparation of a ceramic article using aluminum ferritin analog.

Aluminum ferritin analog gel having a core of aluminum sulfate and aluminum hydroxide was dried at 100° C. and ground into a powder which was dehydrated at 250° C. At 400° C. the protein charred producing a black, carbon-coated powder which burned at 550° C. to a white powder. The powder was calcined at 920° C., with liberation of sulfur trioxide at around 770° C., resulting in partially-sintered, delta-alumina powder which was blended with 2% stearic acid binder and pressed into a 19 mm (¾ inch) diameter disc at about 1700 kilogram/square centimeter (24,000 pounds/square inch) for about 10 minutes. The pressed pellet was sintered at 1200° C. for 3 hours providing a monolithic ceramic disk.

EXAMPLE 9

This example illustrates another preparation of a ceramic article from alumina particles grown in apoferritin.

Dry powder alumina ferritin analog was treated with aqueous ammonia to remove the protein shell from the alumina core; protein separation was effected by centrifugation. The particles were recovered and dried then resuspended in water buffered to pH 4; the slurry was ultracentrifuged at 300 kG for about 9 days. The round-bottomed alumina plug was removed from the centrifuge tube and fired according to the following heat program:

| step | rate | hold temperature | hold time |
|---|---|---|---|
| 1 | 2° C./hr | 140° C. | 1 hour |
| 2 | 2 | 300 | 1 |
| 3 | 2 | 500 | 1 |
| 4 | 2 | 640 | 1 |
| 5 | 5 | 1100 | ½ |
| 6 | −40 | 60 | — |

Figure 1:
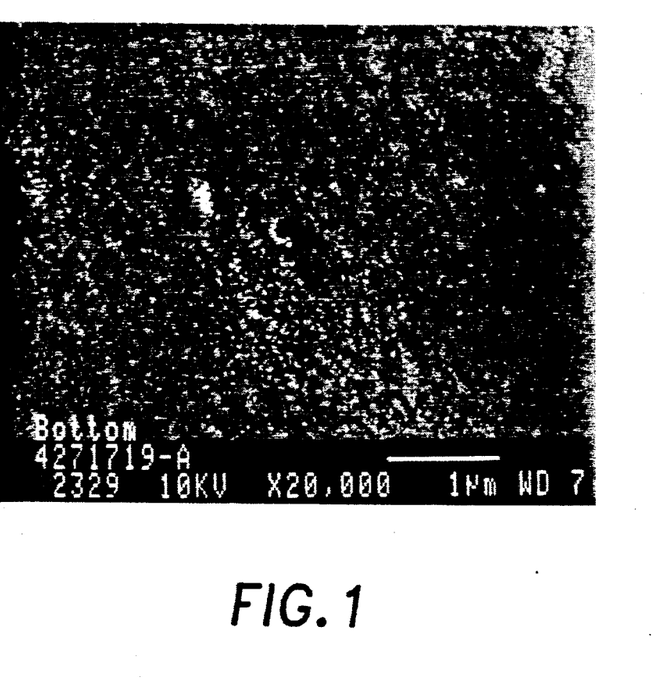
FIG. 1 is a transmission electron micrograph (TEM) using 10 kilovolt electron beam and 20,000× magnification of the surface of a fused, highly uniform, ceramic article prepared from aluminum ferritin analog.

The resulting ceramic was inspected by transmission electron microscopy (FIG. 1) which shows a fused ceramic article comprising 20–80 nanometers (200–800 Angstrom) grains formed from sintering alumina particles of a substantially monomodal particle size distribution of less than 10 nanometers (100 Angstroms), e.g. about 6–8 nanometers (60–80 Angstroms).

EXAMPLE 10

This example illustrates the use of ferritin analog, i.e. aluminum ferritin analog, in providing smooth coatings on the microscopically rough surface of alumina articles.

Figure 2:
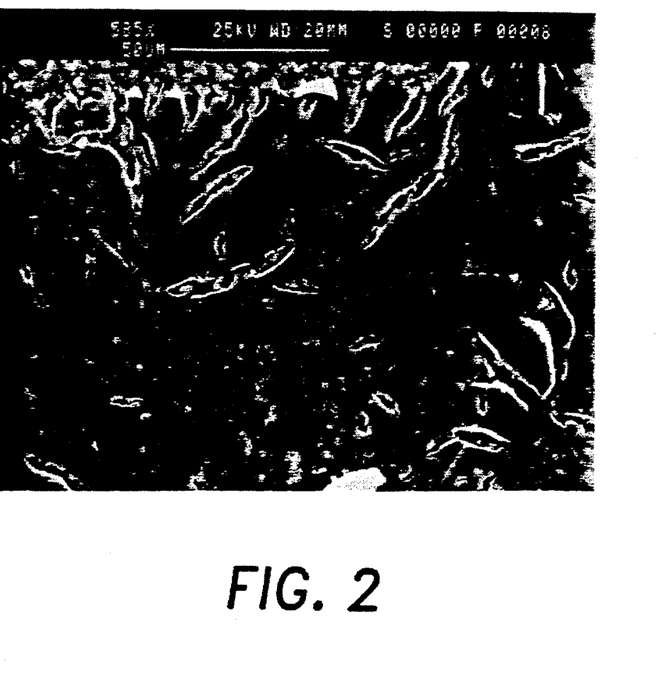
FIGS. 2 and 3 are TEM's of showing a ceramic article having a thin, smooth skin of fused alumina spherules derived from ferritin analog.
Figure 3:
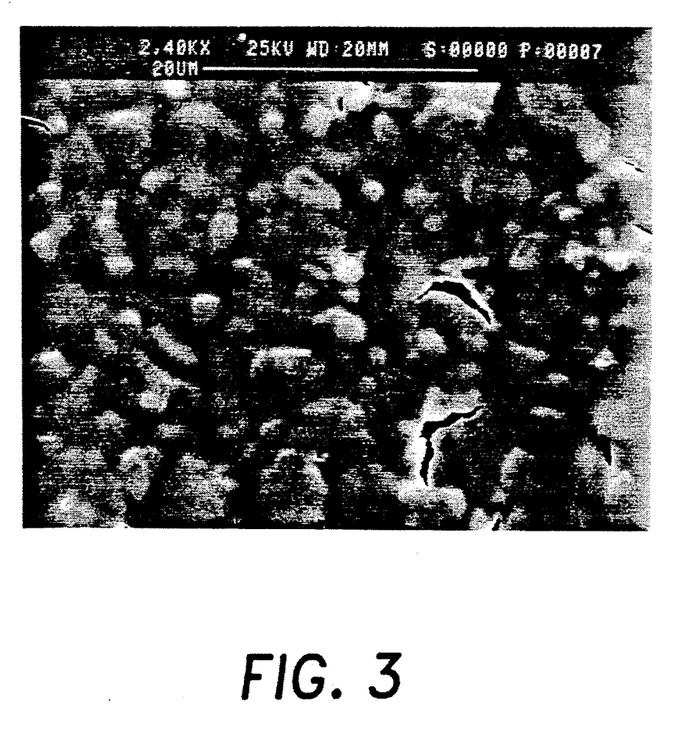

Aluminum ferritin analog was prepared from aluminum nitrate and APOFERRITIN SOLUTION essentially in the manner of Example 4. Aluminum ferritin analog was recovered from about 5 kg of reaction mixture by ultrafiltration and settling. Settled aluminum ferritin analog was centrifuged at 3000 rpm for about 30 minutes yielding a thick white gel which was coated onto two alumina wafers. The wafers were pressed together with the aluminum ferritin analog coated on the inside of the wafers. A weight was placed on the wafers which were fired in a oven heated from about 20° C. to 140° C. at 1° C./min., held at 140° C. for 2 hours then heated to 700° C. at 1° C./min., then held at 700° C. for 1 hour, then cooled in room temperature air. Inspection of FIGS. 2 and 3, TEMs of the coated alumina wafer surface, show that firing of the aluminum ferritin analog burned off the protein and fused the alumina core into a thin, smooth skin layer over the rough surface of the alumina wafer. The aluminum in the ferritin analog sintered at 700° C. which is several hundred degrees below the "normal" sintering temperature of alumina. At sufficiently high voltages, e.g. about 25 kv, the thin alumina skin is sufficiently transparent to the electron beam to clearly show the gross size of the alumina particles comprising the substrate. Where there was insufficient ferritin analog, e.g. at edges as shown at the top of FIG. 2, the coating shrank giving the appearance of tears in the otherwise smooth surface. Tears also appear at various other locations in the smooth alumina skin, see FIG. 3.

EXAMPLE 11

This example illustrates the preparation of a chromium ferritin analog.

About 45 ml of 0.1M HEPES/0.4M ammonium acetate buffer solution (pH 7.8) was added to about 5 g APOFERRITIN SOLUTION (21 mg/ml). After stirring at 40° C. for about 14 hours, 5 ml of chromium(III) acetate (11.1 mg/l Cr) was added in 50–250 microliter portions over a period of nine hours. The chromium/protein solution (pH 5.4) was stirred for about 15 hours at room temperature to produce chromium ferritin analog.

Analysis showed the chromium ferritin analog to have about 1100 chromium atoms per apoferritin shell with core of about 7 nanometers (70 Angstroms) diameter.

EXAMPLE 12

This example illustrates the preparation of silver ferritin analog.

4 g of pH 4 BUFFER SOLUTION was added to 4 l of DI water in an Erlenmeyer flask, followed by 2.7 g of 0.1M sodium chloride solution, 1 g of APOFERRITIN SOLUTION (26 mg/ml) and 2.7 g 0.1M silver nitrate solution, resulting in a slightly cloudy solution. The flask was wrapped in aluminum foil and stored in the dark for 2 weeks resulting in a clear, colorless solution and white precipitate. Analysis indicated no protein in the solution. The precipitate was recovered by decanting and centrifugation in a dark room. Analysis by TEM indicated both large (i.e. micron sized) and ultrafine, i.e. about 5 nanometers (50 Angstrom) particles of silver chloride. The ultrafine particles were in silver ferritin analog; the large particles precipitated and grew in the bulk solution.

EXAMPLE 13

This example illustrates the preparation of manganese ferritin analog.

125.6 mg of manganese(II) acetate tetrahydrate was added to 1.25 ml of APOFERRITIN SOLUTION (1.98 mg/ml), resulting in a clear, colorless solution at pH 7.5. After standing exposed to air for 14 hours at room temperature, the solution became clear and brown from manganese(IV). Analysis of protein showed manganese ferritin analog having a manganese(II) oxide core of about 4 nanometers (40 Angstroms) in diameter.

EXAMPLE 14

This example illustrates the preparation of a therapeutic ferritin analog, i.e. acetaminophen (APAP) ferritin analog.

4.17 g APAP was added to 100 g APOFERRITIN SOLUTION (about 25 mg/ml) heated to about 70° C. and sterile-filtered; the APAP/apoferritin solution was about 4 wt. % APAP having a crystallization temperature of about 55° C. The solution was cooled slowly over an extended time to supersaturation while avoiding the lower crystallization temperature of APAP to cause dissolved APAP to permeate from the supersaturated solution into the apoferritin where APAP can crystallize on nucleation sites on the inside surface of the apoferritin.

Such crystallization inside apoferritin creates a concentration gradient for permeation which reduces the APAP concentration in the solution and, thus, reduces the crystallization temperature of the solution.

The solution was held at 56° C. for 3 days, at 53° C. for 1 day, at 50° C. for 1 day, and finally at 48° C. for 1 day where it became cloudy indicating APAP crystallization in the bulk solution. The solution was then cooled to room temperature; large APAP crystals were removed by a 0.2 micron filter; APAP ferritin analog was separated by a 100,000 MWCO ultrafilter and identified quantitatively by U.V. spectroscopy. The core of APAP ferritin analog was determined to have about 310 APAP molecules.

EXAMPLE 15

This example illustrates the preparation of a calcium ferritin analog, i.e. calcium fluoride ferritin analog. A clear calcium fluoride solution was prepared by dissolving in 500 ml DI water 500 mg starch and 147 mg of calcium chloride dihydrate, then 71 microliters of 49% hydrofluoric acid and followed after about 2 minutes with 20 ml of 0.1N sodium hydroxide. The ferritin analog was prepared by mixing 8 ml of Apoferritin Solution into the calcium fluoride solution. After 2 days analysis showed the calcium fluoride ferritin analog to have about 2,900 calcium atoms per Apoferritin shell with a core of about 9 nanometers (90 Angstroms) in diameter.

EXAMPLE 16

This example illustrates the preparation of a barium sulfate ferritin analog, i.e. barium sulfate ferritin analog.

A slow barium sulfate generating solution was prepared by combining 21.6 ml DI water, 1 ml 11 mM potassium persulfate, 1 ml 11 mM barium nitrate, 1 ml 11 mM sodium thiosulfate pentahydrate, 0.4 ml APOFERRITIN SOLUTION (sodium chloride-free) and 44 microliter 0.1M silver nitrate. The silver nitrate catalyzed the reaction of persulfate and thiosulfate to generate sulfate at a sufficiently slow rate that barium sulfate precipitated inside the apoferritin shell rather than in the bulk solution. After about 2 days TEM analysis indicated barium ferritin analog having about 435 atoms of barium per apoferritin shell in cores smaller than 10 nanometers (100 Angstroms) in diameter.

EXAMPLE 17

This example illustrates the preparation of a uranium ferritin analog.

10 microliters of partially-prepared aluminum ferritin analog was combined with 10 microliters of saturated solution of uranyl acetate. After mixing the solution was allowed to dry and then was analyzed by TEM which showed ferritin analog having cores of about 5 nanometers (50 Angstroms) in diameter and comprising crystalline uranium oxide and amorphous alumina.

EXAMPLE 18

Aluminum ferritin analog (11.2% $Al_2O_3$ on a solids basis) was dried in a vacuum oven at 40° C. to a solid gel. The gel was ground using an alumina motar and pestle into a light yellow powder which was pressed into a pellet in a cylindrical mold (19 mm diameter) at about 5000 kilogram/square centimeter (about 70,000 pounds/square inch) for about 15 minutes. The pressed pellet heated in a furnace according to the following program:

| Step | Rate | Hold Temperature | Hold Time |
| --- | --- | --- | --- |
| 1 | 10° C./min | 240° C. | 1 min |
| 2 | 1 | 330 | 60 |
| 3 | 1 | 400 | 60 |
| 4 | 1 | 480 | 60 |
| 5 | 1 | 600 | 600 |
| 6 | 1 | 1000 | 180 |
| 7 | −5 | 100 | — |

The resulting powdery, low strength pellet was inspected by TEM which showed uniform particles having a substantially monomodal size distribution of about 10 nanometers (100 Angstroms).

What is claimed is:

1. A method of preparing particles comprising:
   (a) combining apoferritin with a medium comprising non-ferrihydrite-forming solute,
   (b) allowing sufficient solute to permeate said apoferritin to form ferritin analogs comprising apoferritin shell surrounding cores substantially devoid of ferrihydrite,
   (c) subjecting said ferritin analog to a disassembling environment to provide apoferritin subunits and cores, and
   (d) recovering said cores as spherules.

2. A method according to claim 1, wherein said disassembling environment is an aqueous medium having a pH between about 1 and 4 or between about 9 and 13.

3. A method according to claim 2 further comprising separating and forming said apoferritin subunits into apoferritin.

* * * * *